United States Patent [19]
Inoue et al.

[11] Patent Number: 5,785,696
[45] Date of Patent: Jul. 28, 1998

[54] DISPOSABLE DIAPER

[75] Inventors: Yasushi Inoue, Kagawa-ken; Tsutomu Kido, Ehime-ken, both of Japan

[73] Assignee: Uni-Charm Corporation, Ehime-ken, Japan

[21] Appl. No.: 592,954

[22] Filed: Jan. 29, 1996

[30] Foreign Application Priority Data

Jan. 31, 1995 [JP] Japan .................. 7-013836

[51] Int. Cl.⁶ ........................................... A61F 13/05
[52] U.S. Cl. .............................................. 604/378
[58] Field of Search ........................... 604/358, 368, 604/372, 378, 385.1

[56] References Cited

U.S. PATENT DOCUMENTS

| | | | |
|---|---|---|---|
| 3,856,012 | 12/1974 | MacDonald et al. | 604/378 |
| 4,988,345 | 1/1991 | Reising | 604/378 |
| 5,334,176 | 8/1994 | Buenger et al. | 604/384 |
| 5,364,382 | 11/1994 | Latimer et al. | 604/378 |
| 5,531,728 | 7/1996 | Lash | 604/378 |
| 5,591,149 | 1/1997 | Cree et al. | 604/381 |

FOREIGN PATENT DOCUMENTS

| | | |
|---|---|---|
| 0343941A2 | 11/1989 | European Pat. Off. . |
| 52-99046 | 1/1951 | Japan . |
| 6-38818 | 5/1994 | Japan . |
| 2055297 | 3/1981 | United Kingdom . |
| 2252047 | 1/1992 | United Kingdom . |
| 2255720 | 11/1992 | United Kingdom . |
| WO 86/05089 | 9/1986 | WIPO . |
| WO 94/06385 | 3/1994 | WIPO . |

*Primary Examiner*—Robert A. Clarke
*Attorney, Agent, or Firm*—Lowe Hauptman Gopstein Gilman & Berner

[57] ABSTRACT

In a disposable diaper having a liquid-absorbent core which comprises, in turn, fluff pulp of less than 70% by weight and superabsorbent polymer particles of 30% or higher by weight, an isolating fibrous layer is placed on an upper surface of the liquid holding layer, then these liquid holding layer and isolating fibrous layer are integrally covered with a liquid-permeable covering layer such as a tissue paper, and these layers are intermittently bonded one to another over the entire extents of the respective laminating surfaces.

11 Claims, 3 Drawing Sheets

DISPOSABLE DIAPER

BACKGROUND OF THE INVENTION

The present invention relates to a disposable diaper used for the absorption and containment of urine and other bodily exudates.

It is well known in disposable diapers to provide a liquid-absorbent core comprising a panel containing fluff pulp and superabsorbent polymer particles and a fibrous web layer overlying the panel so as to provide a cushioning effect and to prevent bodily exudates once absorbed from backward flowing. For example, Japanese Laid-Open Utility Model Application No. Sho52-99046 discloses a disposable absorbent padding according to which a liquid holding layer is composed of pulp fibres and superabsorbent polymer particles of 10 to 60% by weight, then a tissue paper layer and a short fibre fluff layer are successively laminated upon an upper surface of the liquid holding layer and, if necessary, the laminate is entirely covered with a surface material such as a nonwoven fabric to form a liquid-absorbent core. The fluff layer corresponds to the fibrous web layer. In addition, Japanese Patent Publication No. Hei6-38818 discloses a disposable diaper according to which a fluff pulp assembly containing superabsorbent polymer particles is covered with a tissue paper to form a liquid holding layer and a fibrous web layer having a desired compressive elasticity recovery factor is laminated upon an upper surface of the liquid holding layer.

However, in the case of the above-mentioned padding and diaper, the liquid holding layer containing the superabsorbent polymer particles of 30% or higher by weight and the pulp fibres less than 70% by weight has a disadvantage that the polymer particles interfere with adequate intertwining among the pulp fibres and deteriorate a flexibility as well as a shape stability. When the liquid-absorbent core comprising such liquid holding layer is used, the liquid holding layer readily gets loose as the diaper is deformed due to active movements of the baby wearing the padding or the diaper and, as a result, close contacts of the liquid holding layer, the fibrous web layer and the tissue paper may be lost, and this makes a rapid absorption of bodily exudates difficult. Within the liquid holding layer itself, close contacts of interfibres as well as them of the fibres and the polymer particles are deteriorated and a smooth diffusion of bodily exudates within the liquid holding layer is prevented.

SUMMARY OF THE INVENTION

Accordingly, it is a principal object of the invention to solve the above-mentioned problems.

The object set forth above is achieved, according to the invention, by a disposable diaper comprising a liquid-permeable topsheet, a liquid-impermeable backsheet and a liquid-absorbent core disposed between these two sheets, the liquid-absorbent core being composed of a liquid holding layer containing fluff pulp of less than 70% by weight and superabsorbent polymer particles of 30% or higher by weight and an isolating fibrous layer overlying the liquid holding layer, wherein the liquid-absorbent core comprises the liquid holding layer and the isolating fibrous layer integrally covered with a liquid-permeable covering layer; and the liquid holding layer, the isolating fibrous layer and the liquid-permeable covering layer are intermittently bonded one to another substantially over the entire extents of the respective laminating surfaces.

According to an embodiment of the invention, the isolating fibrous layer comprises a melt bond nonwoven fabric and hot melt adhesive is used for the bonding. Preferably, the isolating fibrous layer has a density lower than that of fluff pulp contained by the liquid holding layer. The isolating fibrous layer may be formed by a mixture of hydrophilic fibres and hydrophobic fibres. The liquid-permeable covering layer may be hydrophilic and present a bodily exudates diffusibility higher than that presented by the isolating fibrous layer.

In the disposable diaper described above, there is no apprehension that the liquid-absorbent core might readily get out of shape and the liquid holding layer, the isolating fibrous layer and the liquid-permeable covering layer can be maintained in reliably bonded together even when the liquid holding layer contains relatively much amount of polymer particles, since the liquid holding layer, the isolating fibrous layer and the liquid-permeable covering layer are intermittently bonded one to another substantially over the entire extents of the respective laminating surfaces. Bodily exudates discharged onto the topsheet permeate this, then diffuse in the covering layer, rapidly permeate the isolating fibrous layer into the liquid holding layer by which bodily exudates are absorbed and held. The isolating fibrous layer may serve to keep the liquid holding layer containing bodily exudates absorbed thereby off the wearer's skin.

DESCRIPTION OF THE PREFERRED EMBODIMENT

Figure 1:
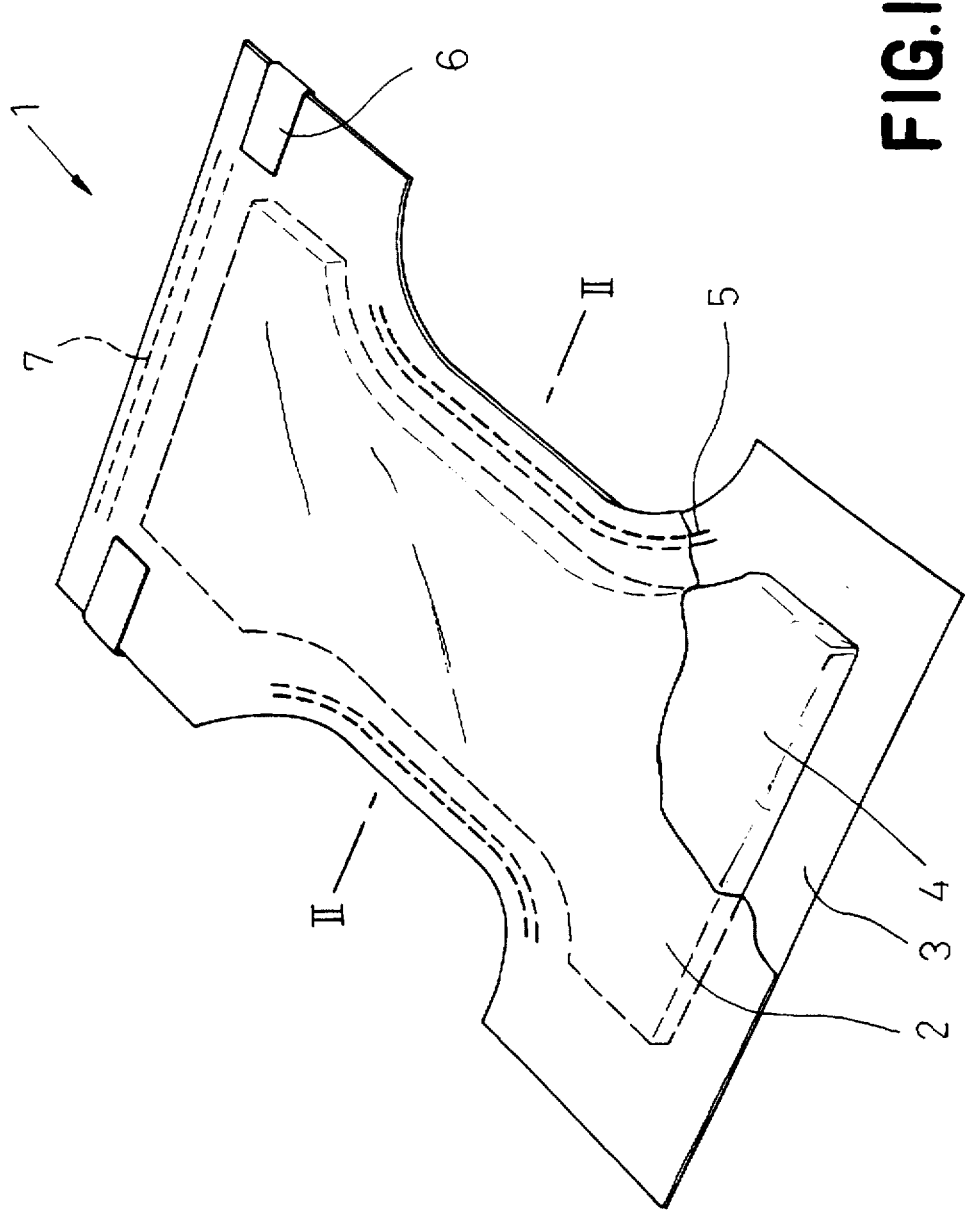
FIG. 1 is a perspective view showing disposable diaper as partially broken away.

Referring to FIG. 1, a diaper 1 comprises a liquid-permeable topsheet 2, a liquid-impermeable backsheet 3, a liquid-absorbent core 4 disposed between these two sheets 2, 3 and elastic members 5 for leg-openings bonded with a tension to inner surface(s) of the topsheet 2 or/and the backsheet 3 along transversely opposite curved side edges of the diaper 1. A rear section of the diaper 1 is provided on its transversely opposite sides with conventional tape fasteners 6 attached thereto and the diaper 1 is further provided along longitudinally opposite ends with elastic members 7 for a waist-opening, which are bonded with a tension to inner surface(s) of the topsheet 2 or/and the backsheet 3.

Figure 2:
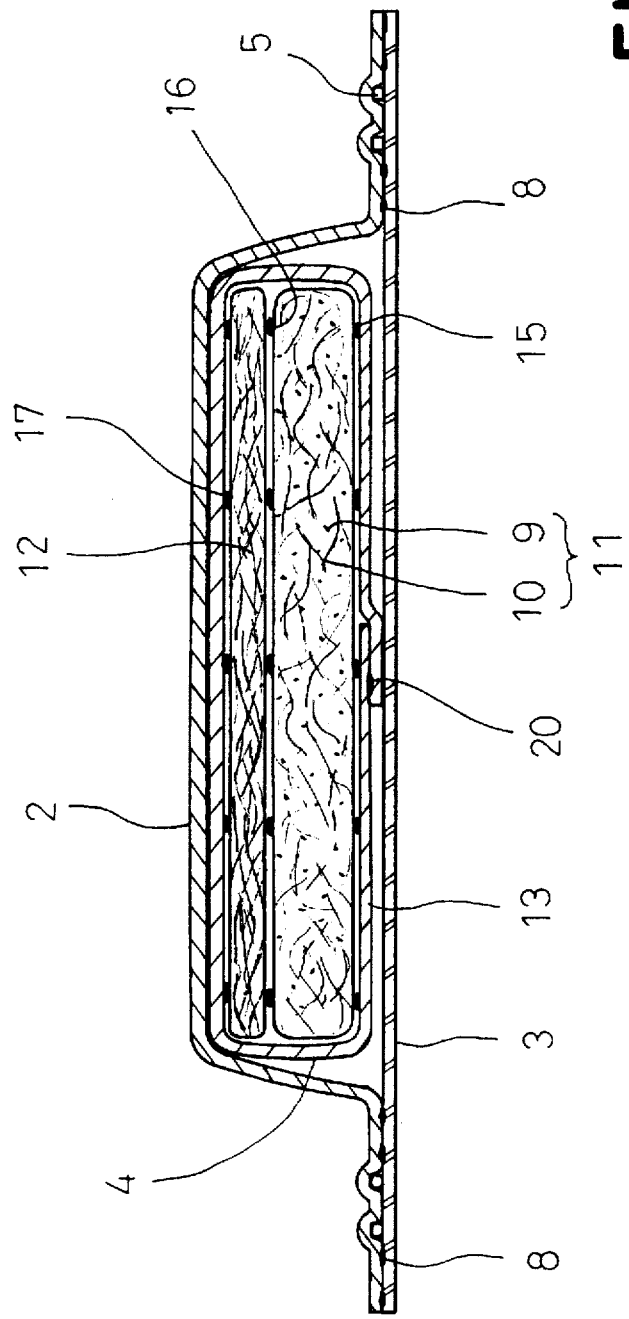
FIG. 2 is a sectional view taken along a line II—II in FIG. 1.
Figure 3C:
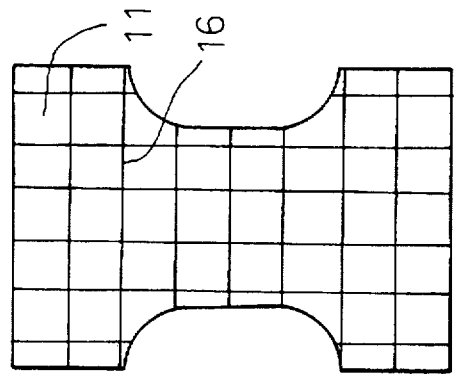
FIG. 3 is a plan view of a liquid holding layer exemplarily showing various adhesive coating patterns (A) through (E).
Figure 3B:
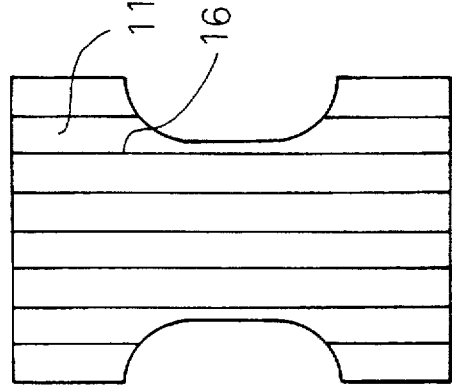
Figure 3A:
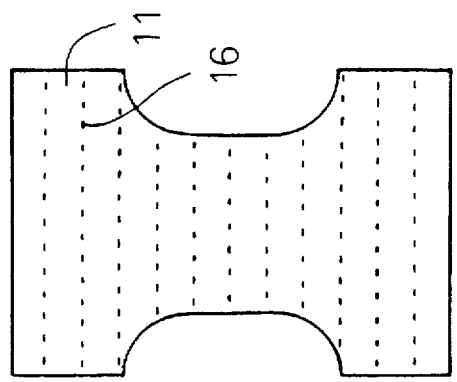
Figure 3E:
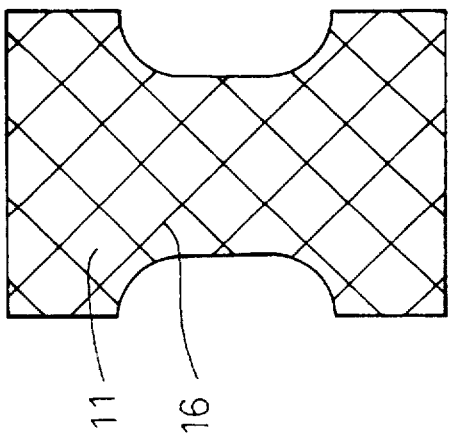
Figure 3D:
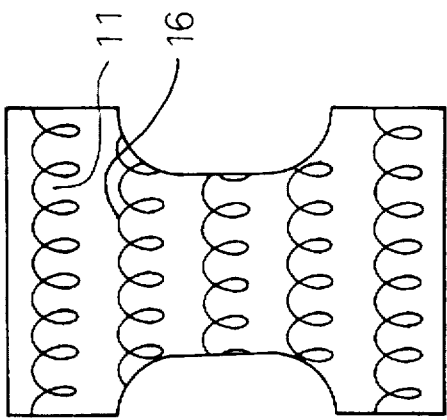

Referring to FIG. 2, the top- and backsheets 2, 3 are placed one upon another along their portions extending outward beyond a peripheral edge of the core 4 and bonded to each other by means of hot melt adhesive 8. The core 4 comprises a liquid holding layer 11 obtained by compression-shaping a mixture of superabsorbent polymer particles 9 of 30% or higher by weight and fluff pulp 10 of less than 70% by weight, an isolating fibrous layer 12 made of a melt bond nonwoven fabric which is identical to the liquid holding layer 11 in shape as well as in size and placed thereon, and a liquid-permeable covering layer 13 such as a tissue paper integrally covering these two layers 11, 12. These liquid holding layer 11, isolating fibrous layer 12 and covering layer 13 are laminated together and bonded together by hot melt adhesive 15, 16, 17 intermittently and evenly applied on respective laminating surfaces.

As shown in FIG. 3, the adhesive 15, 16, 17 may be of various patterns. The liquid holding layer 11 is hourglassshaped and the adhesive 15, 16, 17 may be applied in spotted (A), vertically striped (B), latticed (C) and (D), or spiral (E) pattern.

When a plurality of continuous lines are described by the adhesive 15, 16, 17 each pair of adjacent lines must be spaced from each other sufficiently to ensure that diffusion and permeation of the bodily exudates are not interfered by them. Relative to an area of the liquid holding layer 11, the adhesive 15, 16, 17 is applied preferably over 2 to 30%, more preferably 5 to 20% thereof, respectively.

In the diaper 1 of the invention, the top- and backsheets 2, 3 may be made of materials usually used in the relevant technical field. The liquid holding layer 11 may be mixed with thermoplastic synthetic fibres of up to 20% by weight not only to improve a bodily exudates diffusibility within the layer but also to allow the liquid holding layer 11 to be thermally shaped. The isolating fibrous layer 12 may serve to isolate the topsheet 4 from the liquid holding layer 11 and thereby may suppress back flow and exudation of the bodily exudates once absorbed by the liquid holding layer 11 into the topsheet 2 when the core 4 is pressed against the wearer and provides the core 4 with a desired cushioning nature so as to alleviate a stiff touch of the hard polymer particles 9 and simultaneously to prevent the particles 9 from breaking through the covering layer 13. Additionally, the isolating fibrous layer 12 facilitates bodily exudates to diffuse in the horizontal direction of the core 4. The isolating fibrous layer 12 may be made of hydrophilic synthetic fibres or a mixture of such fibres and hydrophobic thermoplastic synthetic fibres. While the isolating fibrous layer 12 may be preferably formed by a melt bond nonwoven fabric, it is also possible to replace the nonwoven fabric by a fibrous web having been subjected only to carding. The covering layer 13 comprises a hydrophilic material such as wood pulp or rayon fibres as its main ingredient. The covering layer 13 is preferably adapted to present a bodily exudates diffusibility higher than that presented by the fibrous web layer 12 and to cover the entire surface of the core 4 so that the polymer particles 9 may be reliably confined therein. To this end, transversely opposite side edges of the covering layer 13 may be put one upon another and bonded together on the bottom side of the liquid holding layer 11 by means of hot melt adhesive or, though not shown, longitudinally opposite ends thereof may be put one upon another and bonded together. Alternatively, an appropriate sheet material may be disposed between the bottom surface of the liquid holding layer 11 and the covering layer 13 to prevent the polymer particles 9 from breaking through the covering layer 13 underlying the liquid holding layer 11. A density of the fibrous web layer 12 may be adjusted to be higher than that of the pulp 10 to facilitate bodily exudates to move downward.

In the disposable diaper of the invention, the liquid holding layer, the isolating layer and the covering layer laminated together to form the liquid-absorbent core are intermittently bonded one to another over the entire extents of the respective laminating surfaces so that these laminated layers can be maintained in a reliably bonded state even if the diaper put on the wearer's body is curved or distorted. Relatively much amount of superabsorbent polymer particles can be used without an apprehension that the liquid holding layer might become less flexible and readily get loose, resulting in getting out of shape. In this manner, the inventive diaper can maintain a desired absorptivity and comfortableness to wear it even if relatively much amount of the superabsorbent polymer particles are used.

What is claimed is:

1. A disposable diaper comprising a liquid-permeable topsheet, a liquid-impermeable backsheet and a liquid-absorbent core disposed between said topsheet and backsheet, said liquid-absorbent core including a liquid holding layer containing fluff pulp and superabsorbent polymer particles and an isolating fibrous layer overlying said liquid holding layer, wherein:

said liquid-absorbent core further includes a liquid-permeable covering layer wrapped around to cover said liquid holding layer and said isolating fibrous layer; and wherein said liquid holding layer, said isolating fibrous layer and said liquid-permeable covering layer are intermittently bonded together substantially over an entire extent of respective laminating surfaces thereof to thereby jointly constitute a laminated structure.

2. A diaper according to claim 1, wherein said isolating fibrous layer comprises a melt bond nonwoven fabric and hot melt adhesive is used for said bonding.

3. A diaper according to claim 1, wherein said isolating fibrous layer has a density lower than that of fluff pulp contained by said liquid holding layer.

4. A diaper according to claim 1, wherein said isolating fibrous layer is formed by a mixture of hydrophilic fibres and hydrophobic fibres.

5. A diaper according to claim 1, wherein said liquid-permeable covering layer is hydrophilic and presents a bodily exudates diffusibility higher than that presented by said isolating fibrous layer.

6. A diaper according to claim 1, wherein said liquid-permeable covering layer is made of a tissue paper.

7. The disposable diaper of claim 1, wherein said liquid holding layer contains said fluff pulp being of less than 70% by weight and said superabsorbent polymer particles being about 30% or greater by weight.

8. The diaper according to claim 1, wherein said liquid absorbent core is not bonded to said topsheet.

9. The diaper of claim 1, wherein said liquid-permeable covering layer is not bonded to said topsheet.

10. The diaper of claim 1, wherein the liquid holding layer and said isolating fibrous layer are approximately the same width.

11. A disposable diaper comprising a liquid-permeable topsheet, a liquid-impermeable backsheet and a liquid-absorbent core disposed between said topsheet and backsheet, said liquid-absorbent core including a liquid holding layer and a separate isolating fibrous layer overlying said liquid holding layer, wherein said liquid-absorbent core further includes a liquid-permeable covering layer wrapped around to cover said liquid holding layer and said isolating fibrous layer, and wherein said liquid holding layer, said isolating fibrous layer and said liquid-permeable covering layer are intermittently bonded together with adhesive disposed at respective facing surfaces thereof.

* * * * *